(12) United States Patent
Kim et al.

(10) Patent No.: US 10,661,252 B2
(45) Date of Patent: May 26, 2020

(54) CATALYST FOR PREPARING 2,5-FURANCARBOXYLIC ACID AND A METHOD FOR PREPARING 2,5-FURANCARBOXYLIC ACID USING THE CATALYST

(71) Applicant: KOREA INSTITUTE OF INDUSTRIAL TECHNOLOGY, Cheonan-si, Chungcheongnam-do (KR)

(72) Inventors: Yong Jin Kim, Cheonan-si (KR); Jin Ku Cho, Yongin-si (KR); Seung Han Shin, Seoul (KR); Hong Shik Lee, Cheonan-si (KR); Dinesh Kumar Mishra, Cheonan-si (KR)

(73) Assignee: Korea Institute of Industrial Technology, Cheonan-si, Chungcheongnam-do (KR)

( * ) Notice: Subject to any disclaimer, the term of this patent is extended or adjusted under 35 U.S.C. 154(b) by 64 days.

(21) Appl. No.: 16/082,918

(22) PCT Filed: Mar. 7, 2017

(86) PCT No.: PCT/KR2017/002462
§ 371 (c)(1),
(2) Date: Sep. 6, 2018

(87) PCT Pub. No.: WO2017/155286
PCT Pub. Date: Sep. 14, 2017

(65) Prior Publication Data
US 2019/0083960 A1    Mar. 21, 2019

(30) Foreign Application Priority Data
Mar. 7, 2016    (KR) .................. 10-2016-0026921

(51) Int. Cl.
*B01J 23/46* (2006.01)
*C07D 307/48* (2006.01)
(Continued)

(52) U.S. Cl.
CPC .......... *B01J 23/462* (2013.01); *B01J 23/005* (2013.01); *B01J 23/38* (2013.01); *B01J 23/42* (2013.01);
(Continued)

(58) Field of Classification Search
CPC ........ B01J 23/462; B01J 23/005; B01J 23/38; B01J 23/42; B01J 23/44; B01J 23/46;
(Continued)

(56) References Cited

U.S. PATENT DOCUMENTS 7,119,225 B1 * 10/2006 Herron ................ B01J 23/52
562/400
7,829,140 B1    11/2010 Zhong et al.
(Continued)

FOREIGN PATENT DOCUMENTS

| CN | 103724303 A | 4/2014 |
|---|---|---|
| CN | 104607202 A | 5/2015 |
| KR | 10-2015-0133388 A | 11/2015 |

OTHER PUBLICATIONS

Liu et al (Aerobic oxidation of 5-hydroxymethylfurfural into 2,5-furandicarboxylic acid in water under mild conditions, Green Chem, (2015) 17, 1610-1617) (Year: 2015).*
(Continued)

Primary Examiner — Melvin C. Mayes
Assistant Examiner — Michael Forrest
(74) Attorney, Agent, or Firm — Rabin & Berdo, P.C.

(57) ABSTRACT

The present invention relates to a carboxylation catalyst, which catalyzes carboxylation of a furan-based compound containing a hydroxyl group and a carbonyl group or a
(Continued)

derivative thereof to prepare 2,5-furandicarboxylic acid (FDCA), and is configured as a spinel support, and noble metal nanoparticles incorporated into the spinel support selected from the group consisting of $MnCo_2O_4$, $CoMn_2O_4$, and combinations thereof, and to a method of preparing 2,5-furandicarboxylic acid (FDCA), including providing a carboxylation catalyst configured such that noble metal nanoparticles are incorporated into a spinel support; and carboxylating a furan-based compound containing a hydroxyl group and a carbonyl group or a derivative thereof in the presence of the carboxylation catalyst.

16 Claims, 6 Drawing Sheets

(51) Int. Cl.

| | | |
|---|---|---|
| *B01J 32/00* | (2006.01) | |
| *B01J 23/38* | (2006.01) | |
| *B01J 23/44* | (2006.01) | |
| *B01J 23/42* | (2006.01) | |
| *B01J 35/02* | (2006.01) | |
| *B01J 23/00* | (2006.01) | |
| *B01J 35/00* | (2006.01) | |
| *C07D 307/68* | (2006.01) | |

(52) U.S. Cl.
CPC ............... *B01J 23/44* (2013.01); *B01J 23/46* (2013.01); *B01J 32/00* (2013.01); *B01J 35/006* (2013.01); *B01J 35/02* (2013.01); *B01J 35/026* (2013.01); *C07D 307/48* (2013.01); *C07D 307/68* (2013.01); *B01J 2523/17* (2013.01); *B01J 2523/22* (2013.01); *B01J 2523/27* (2013.01); *B01J 2523/31* (2013.01); *B01J 2523/47* (2013.01); *B01J 2523/72* (2013.01); *B01J 2523/842* (2013.01); *B01J 2523/845* (2013.01)

(58) Field of Classification Search
CPC . B01J 32/00; B01J 35/006; B01J 35/02; B01J 35/026; C07D 307/48; C07D 307/68
See application file for complete search history.

(56) References Cited

U.S. PATENT DOCUMENTS

| | | | |
|---|---|---|---|
| 2009/0124834 A1* | 5/2009 | Wang | B01J 23/8906 564/422 |
| 2011/0092720 A1 | 4/2011 | Yutaka et al. | |
| 2012/0059178 A1* | 3/2012 | Sanborn | C07D 307/68 549/485 |

OTHER PUBLICATIONS

Kang et al (From Lignocellulosic Biomass to Furans via 5-acetoxymethylfurfural as an Alternative to 5-Hydroxymethylfurfural, ChemSusChem (2015), 8, 1179-1188) . (Year: 2015).*
Wei-Zhen Li et al., "Stable platinum nanoparticles on specific $MgAl_2O_4$ spinel facets at high temperatures in oxidizing atmospheres", Nature Communications, Dec. 1, 2013, pp. 1-8.
Juan M. Campelo et al., "Sustainable Preparation of Supported Metal Nanoparticles and Their Applications in Catalysis", Chemsuschem, Jan. 26, 2009, pp. 18-45, vol. 2.
Extended European Search Report dated Nov. 29, 2019.
European Formal Notification dated Dec. 17, 2019.
Gorbanev, Yury Y., et al., "Selective Aerobic Oxidation of 5-hydroxymethylfurfural in Water over Solid Ruthenium Hydroxide Catalysts with Magnesium-based Supports", Catalysis Letters, 2011, pp. 1752-1760, vol. 141, No. 12.
Zhang, Zehui et al., "Recent Advances in the Catalytic Synthesis of 2, 5-furandicarboxylic Acid and Its Derivatives", ACS Catalysis, 2015, pp. 6529-6544, vol. 5, No. 11.
Gorbanev, Yury Y., et al., "Effect of Support in Heterogeneous Ruthenium Catalysts Used for the Selective Aerobic Oxidation of HMF in Water", Topics in Catalysis, 2011, pp. 1318-1324, vol. 43 Nos. 16-18.
Wan, Xiaoyue et al., "Base-free Aerobic Oxidation of 5-hydroxymethylfurfural to 2, 5-furandicarboxylic Acid in Water Catalyzed by Functionalized Carbon Nanotube-supported Au-Pd Alloy Nanoparticles", ACS Catalysis, 2014, pp. 2175-2185, vol. 4, No. 7.
Mishra, Dinesh Kumar et al., "MnCo2O4 Spinel Supported Ruthenium Catalyst for Air-oxidation of HMF to FDCA under Aqueous Phase and Base-free Conditions", Green Chemistry, 2017, pp. 1619-1623, vol. 19, No. 7.

* cited by examiner

CATALYST FOR PREPARING 2,5-FURANCARBOXYLIC ACID AND A METHOD FOR PREPARING 2,5-FURANCARBOXYLIC ACID USING THE CATALYST

TECHNICAL FIELD

The present invention relates to a method of preparing 2,5-furandicarboxylic acid from a furan-based compound containing a hydroxyl group and a carbonyl group or a derivative thereof using a catalyst configured such that noble metal nanoparticles are incorporated into a spinel-type support.

BACKGROUND ART

In recent years, many scientists and researchers have shown considerable interest in biomass-derived molecules, known as platform molecules or building blocks.

Typical examples of such platform molecules may include 5-hydroxymethyl-2-furfural (hereinafter referred to as HMF), which is recently receiving attention as a biomass-derived furan-based compound, and 2,5-furandicarboxylic acid (hereinafter referred to as FDCA), produced by an oxidation reaction on HMF.

In particular, FDCA, which is a platform molecule, is structurally similar to terephthalic acid, serving as a raw material of polyester, which is a typical polymer, and may thus be used as an alternative to terephthalic acid. Furthermore, an FDCA-based polymer, for example, poly(ethylene-2,5-furandicarboxylate) (PEF), has also been studied as an alternative polymer to polyethylene terephthalate (PET).

U.S. Patent Publication (US 2012/0059178 A1) discloses a process for oxidation of furan aldehyde such as HMF using a Co/Mn binary catalyst system. Here, the use of Co/Mn and MEK (methyl ethyl ketone) as a catalyst causes selective oxidation into DFF, and the use of Co/Mn and bromide as a catalyst causes selective oxidation into 2,5-furandicarboxylic acid (hereinafter referred to as FDCA).

Also, U.S. Patent Publication (US 2011/0092720 A1) discloses a method of preparing FDCA, which produces FDCA having high purity at high yield, comprising bringing HMF into contact with an oxidizing agent in an organic acid (solvent) in the presence of bromine and a metal catalyst and allowing HMF to react with the oxidizing agent. These methods allow the reaction to proceed while removing the water produced by the reaction, and the yield of FDCA is about 62%.

However, the above methods are problematic because the preparation process is complicated or high temperature and pressure have to be used, the purity and productivity of final products are low, and, upon preparation of FDCA, oxidation does not completely occur, and thus byproducts other than FDCA, for example, 5-hydroxymethyl-2-furancarboxylic acid (HMFCA), 5-formyl-2-furancarboxylic acid (FFCA), 2,5-diformylfuran (DFF), and the like, may be generated. Hence, improvements in processes for selective oxidation of FDCA are continually required.

CITATION LIST

Patent Literature

U.S. Patent Publication No. 2012/0059178
U.S. Patent Publication No. 2011/0092720

DISCLOSURE

Technical Problem

Accordingly, the present invention is intended to provide a method of preparing FDCA, in which FDCA having high purity may be produced at high yield from a furan-based compound containing a hydroxyl group and a carbonyl group or a derivative thereof in a simple manner under conditions of low temperature and low air pressure while minimizing the generation of byproducts.

Technical Solution

Based on the results of extensive and intensive research into solving the above problems by the present inventors, an aspect of the present invention provides a catalyst for preparing FDCA, which is a catalyst for carboxylation of a furan-based compound containing a hydroxyl group and a carbonyl group or a derivative thereof and is configured such that noble metal nanoparticles are incorporated into a spinel-type support.

Another aspect of the present invention provides a method of preparing FDCA, comprising carboxylating a furan-based compound containing a hydroxyl group and a carbonyl group or a derivative thereof using a catalyst configured such that noble metal nanoparticles are incorporated into a spinel-type support.

Furthermore, the furan-based compound containing a hydroxyl group and a carbonyl group or the derivative thereof, which is used in the method of preparing FDCA according to the present invention, may be obtained from biomass containing cellulose or polysaccharides, but is not limited thereto.

Advantageous Effects

According to the present invention, the use of the catalyst configured such that noble metal nanoparticles are incorporated into a spinel-type support enables the preparation of FDCA at high selectivity and high yield at low temperature and low air pressure under base-free conditions without the use of an additional base material and without complicated processing, unlike conventional techniques. As such, the generation of byproducts can be minimized.

MODE FOR INVENTION

An embodiment of the present invention pertains to a catalyst for preparing 2,5-furandicarboxylic acid (FDCA), which is a catalyst for carboxylation of a furan-based compound containing a hydroxyl group and a carbonyl group or a derivative thereof and is configured such that noble metal nanoparticles are incorporated into a spinel-type support.

Here, the spinel-type support may be at least one selected from the group consisting of $MnCo_2O_4$, $CoMn_2O_4$, $ZnAl_2O_4$, $FeAl_2O_4$, $CuFe_2O_4$, $ZnMn_2O_4$, $MnFe_2O_4$, $Fe_3O_4$, $TiFe_2O_4$, $ZnFe_2O_4$, $Mg_2SiO_4$, and $Fe_2SiO_4$, and in an embodiment of the present invention, the spinel-type support may be $MnCo_2O_4$ or $CoMn_2O_4$.

Figure 1:
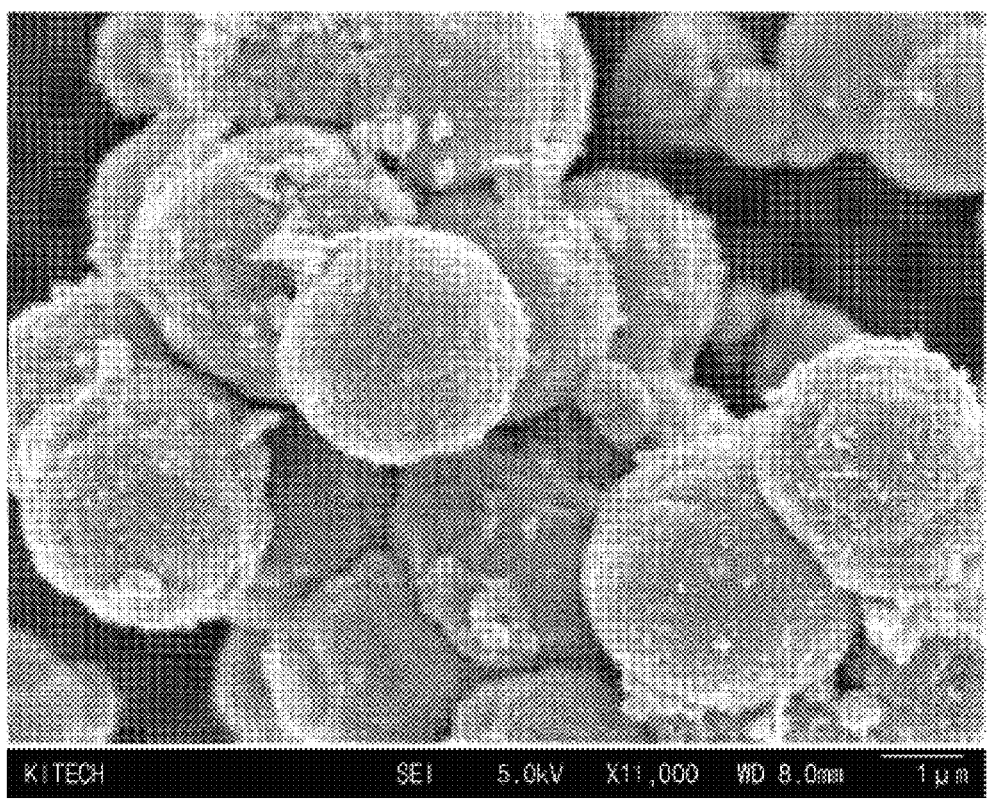
FIG. 1 is an SEM image showing a spinel support according to an embodiment of the present invention.
Figure 2:
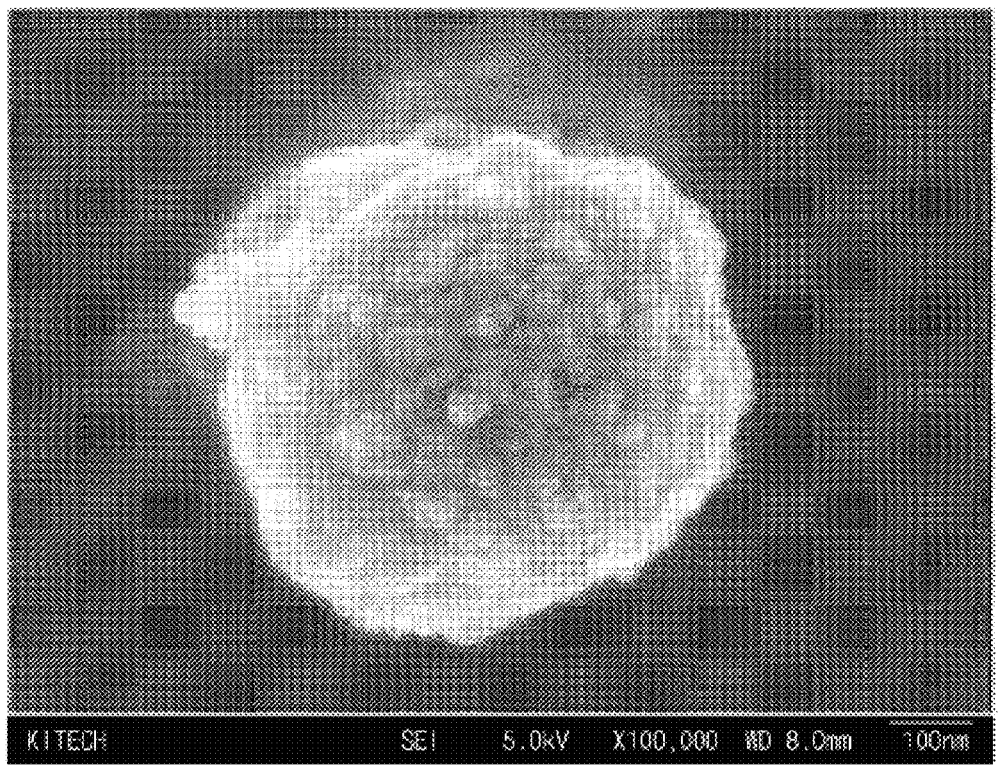
FIG. 2 is an SEM image showing microspheres of a spinel-type $MnCo_2O_4$ support according to an embodiment of the present invention.

As shown in FIG. 1, representing the results of SEM of $MnCo_2O_4$, the $MnCo_2O_4$ or $CoMn_2O_4$ support has a spinel structure with an average particle size ($D_{50}$) of 2.0 to 4.0 μm, the structure being configured such that a plurality of microspheres ranging from 30 to 60 nm in size is aggregated, as shown in FIG. 2.

Figure 3:
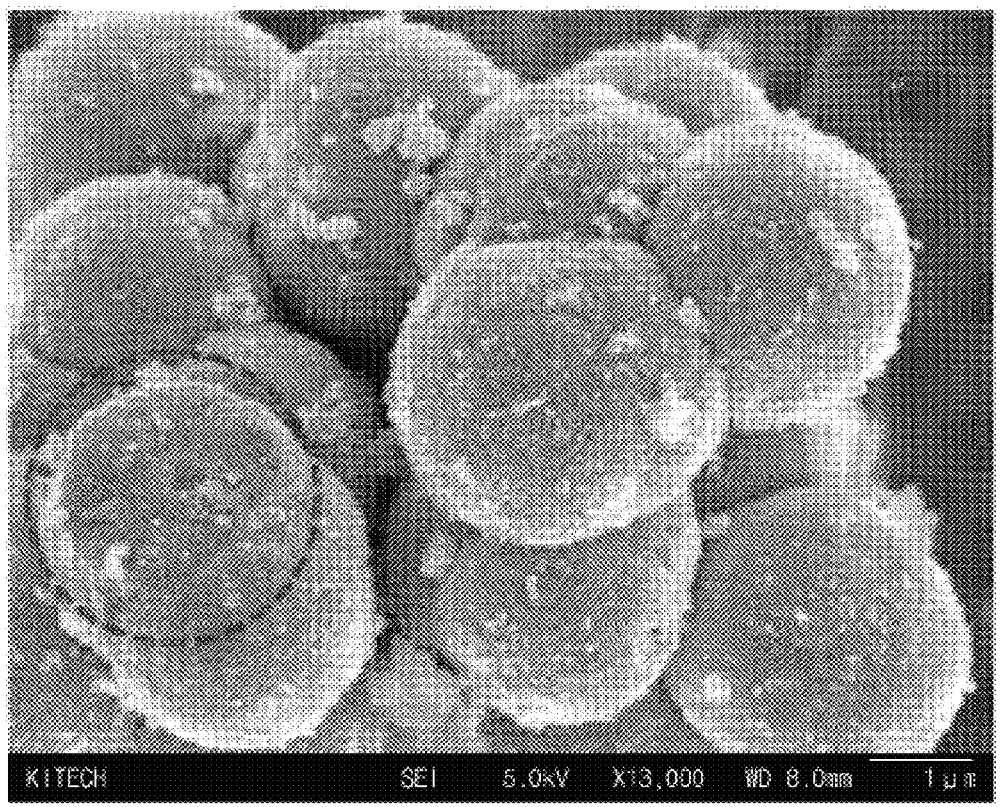
FIG. 3 is an SEM image showing a plurality of pores in the spinel-type $MnCo_2O_4$ support according to an embodiment of the present invention.

As shown in the dotted line of FIG. 3, the $MnCo_2O_4$ support may contain therein a plurality of pores, and the noble metal nanoparticles may be incorporated into the support.

In an embodiment of the present invention, the $MnCo_2O_4$ or $CoMn_2O_4$ support has the specific structure and size shown in FIGS. 1 to 3, and thus, when noble metal nanoparticles are reduced and thus incorporated into the support, an efficient configuration in which the nanoparticles are uniformly distributed in the support may result.

The noble metal may be at least one selected from the group consisting of platinum, palladium, and ruthenium, and in an embodiment of the present invention, the noble metal may be ruthenium.

In particular, the noble metal nanoparticles may have a particle size of 5 to 15 nm, and the noble metal nanoparticles having a size of 5 to 15 nm may be efficiently incorporated into the spinel-type support. Furthermore, the noble metal particles are uniformly dispersed in the structure of the spinel support in which a plurality of microspheres is aggregated, thereby inducing stable oxidation of the furan-based compound.

Also, the noble metal nanoparticles may be used in an amount of 0.1 to 10 wt % based on the total weight of the catalyst including the support and the noble metal nanoparticles. If the amount of the noble metal nanoparticles is less than 0.1 wt %, the yield of 2,5-furandicarboxylic acid (FDCA) may decrease. On the other hand, if the amount thereof exceeds 10 wt %, the furan-based compound may be drastically oxidized and thus processing stability may become problematic, and excessive use of noble metal particles may increase the price of the catalyst, thus negating economic benefits.

The method of preparing the spinel-type support is not particularly limited, and typical methods known in the art may be used. Also, the method of loading the noble metal nanoparticles into the spinel-type support is not particularly limited, but according to an embodiment of the present invention, the spinel-type support is impregnated with a noble metal salt hydrate in an aqueous solution phase, followed by reducing treatment, whereby the reduced noble metal is incorporated into the support.

When the catalyst according to an embodiment of the present invention is used, efficient oxidation from HMF into FDCA may occur upon preparation of FDCA, and the preparation process may be performed at low temperature and low air pressure under base-free conditions without the use of an additional base material, unlike conventional techniques.

Another aspect of the present invention pertains to a method of preparing 2,5-furandicarboxylic acid (FDCA), comprising carboxylating a furan-based compound containing a hydroxyl group and a carbonyl group or a derivative thereof in the presence of a catalyst configured such that noble metal nanoparticles are incorporated into a spinel-type support.

The spinel-type support may be at least one selected from the group consisting of $MnCo_2O_4$, $CoMn_2O_4$, $ZnAl_2O_4$, $FeAl_2O_4$, $CuFe_2O_4$, $ZnMn_2O_4$, $MnFe_2O_4$, $Fe_3O_4$, $TiFe_2O_4$, $ZnFe_2O_4$, $Mg_2SiO_4$, and $Fe_2SiO_4$, and in an embodiment of the present invention, the spinel-type support may be $MnCo_2O_4$ or $CoMn_2O_4$.

Here, the furan-based compound containing a hydroxyl group and a carbonyl group may be 5-hydroxymethylfurfural (HMF).

In the present invention, the furan-based compound, particularly HMF, may be obtained through dehydration of sugar, especially hexose, for example, fructose and glucose, and the sugar may be obtained through hydrolysis of biomass containing cellulose or polysaccharides and possibly from glucose and fructose (high-sugar-content syrup) resulting from isomerization of glucose. Briefly, the furan-based compound used in the present invention may be regarded as being obtained from biomass containing cellulose or polysaccharides. The biomass containing cellulose or polysaccharides is an example of widely available natural materials, and is a renewable material for HMF.

In another embodiment of the present invention, useful as a substrate for producing FDCA, a derivative of a furan-based compound containing a hydroxyl group and a carbonyl group may include a furan-based compound containing an acyloxy group and a carbonyl group. Specific examples thereof may include acetoxymethylfurfural (AMF), in which the hydroxyl group of HMF is substituted with an acetyloxy group.

In the method of preparing FDCA according to the present invention, minimizing the yields of DFF and FFCA and maximizing the yield of FDCA were realized depending on changes in the catalyst, solvent, and pressure and temperature conditions.

The noble metal nanoparticles may be at least one selected from the group consisting of platinum, palladium, and ruthenium. In the catalyst configured such that noble metal nanoparticles are incorporated into the spinel-type support, the molar ratio of the noble metal nanoparticles to the furan-based compound preferably falls in the range of 1:5-200, and more preferably 1:10-150, in order to realize efficient processing while maximizing the conversion of HMF and the yield of FDCA by optimizing the proportion of the noble metal.

The oxidation of the furan-based compound is preferably carried out under conditions of an air pressure of 80 to 1000 psi in the reactor, a reaction temperature of 100 to 200° C. and a reaction time of 3 to 12 hr, and more preferably an air pressure of 100 to 500 psi, a reaction temperature of 120 to 150° C., and a reaction time of 5 to 10 hr. If the air pressure is less than 80 psi, the yield of FDCA and the amount of the final product are low. On the other hand, if the air pressure exceeds 1000 psi, the yield of FDCA is not significantly increased, but production and processing costs and processing simplicity under the low air pressure conditions desired in the present invention may become unfavorable due to excessively high pressure, and furthermore, byproducts may be generated in large amounts due to excessive air supply. If the reaction time is less than 3 hr, the yield of FDCA is low. On the other hand, if the reaction time exceeds 12 hr, the yield of byproducts and processing costs may increase. Also, if the reaction temperature is lower than 100° C., the yield of FDCA is low. On the other hand, if the reaction temperature is higher than 200° C., the process cannot be efficiently conducted in the low temperature range desired in the present invention.

For example, various compounds may be produced depending on the extent of oxidation of HMF, as represented in Scheme 1 below.

is a compound desired in the present invention. Hence, according to an embodiment of the present invention, water may be used as the solvent upon preparation of FDCA. When water is used as the solvent in this way, the generation of byproducts may be minimized, and the selectivity of FDCA may increase. Moreover, in an embodiment of the present invention, a base-free oxidation process may be carried out under mild conditions, without the use of a base material, for example, NaOH or $Na_2CO_3$, which is conventionally contained in the solvent to oxidize FDCA.

Also, the reaction may be carried out in a single vessel.

A better understanding of the present invention will be given through the following examples, which are set forth to more specifically describe the present invention but are not to be construed as limiting the scope of the present invention.

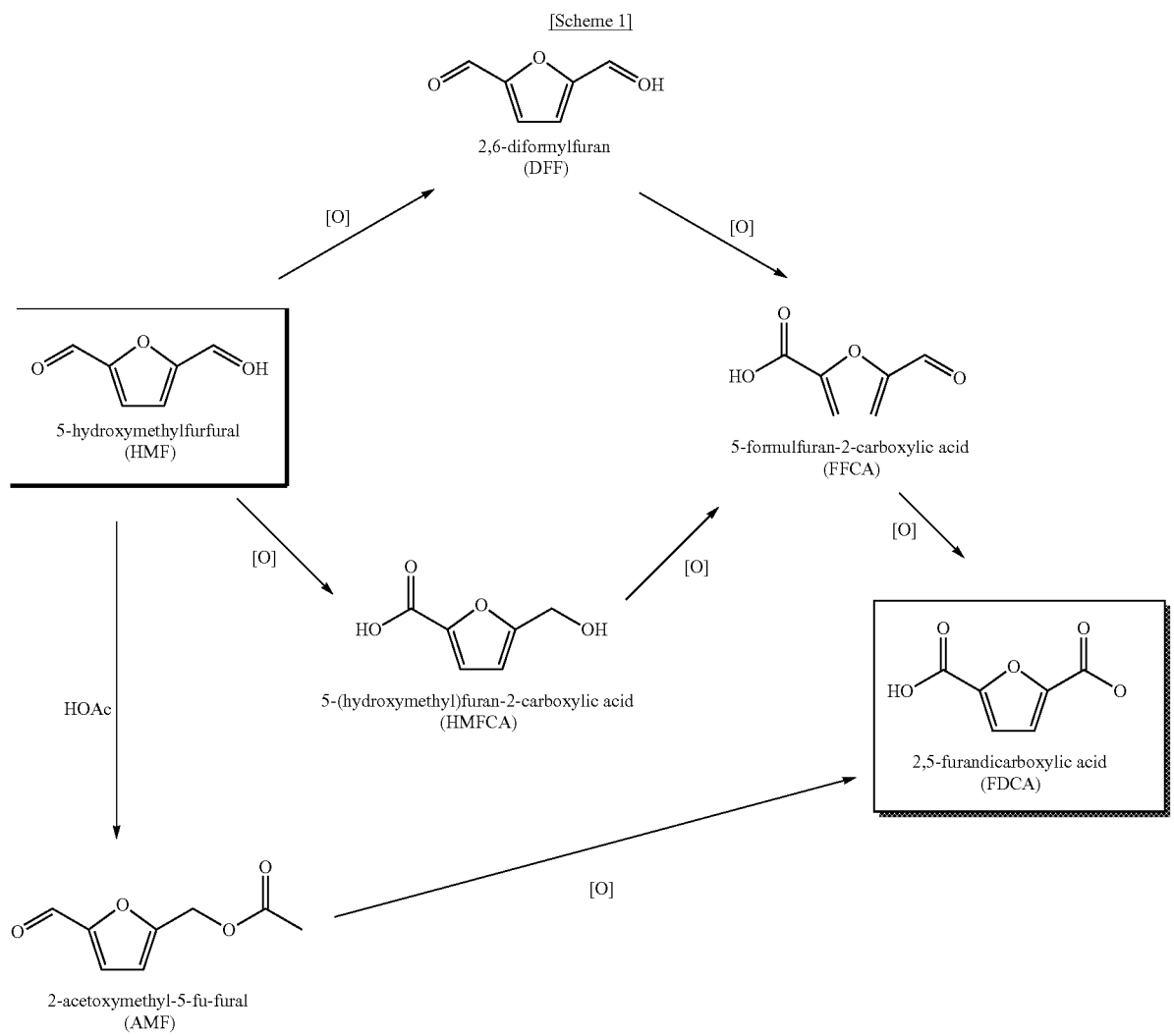

[Scheme 1]

In the preparation of FDCA from HMF using the catalyst according to an embodiment of the present invention, HMFCA, FFCA, DFF, and the like are regarded as byproducts because the extent of oxidation thereof is different from that of the finally obtained FDCA. Also, the produced HMFCA has very low solubility in the solvent and may thus have an adverse influence on the final yield of FDCA, which Preparation of Spinel-Type $MnCo_2O_4$ Support As commercially available materials, 65.3 mmol of $(CH_3COO)_2Co.4H_2O$ and 32.6 mmol of $(CH_3COO)_2Mn.4H_2O$ (a molar ratio of Co:Mn=2:1) were dissolved in 400 mL of water and stirred for 30 min to thus homogenize the mixture.

Separately, 50 g of ammonium sulfate was dissolved in 400 mL of water. The resulting solution was slowly stirred and mixed for 4 hr. The sufficiently dissolved aqueous solution of $NH_4HCO_3$ was then slowly mixed with the above solution, followed by stirring for 6 hr. Thereafter, the precipitate having a pale pink color was obtained through filtration, and was then washed with distilled water and anhydrous ethanol, followed by drying at 60° C. for 12 hr. The obtained carbonate precursor was thermally treated in a furnace at 425° C. (2° C./min) for 12 hr while air was supplied thereto, and was then slowly cooled to room temperature and maintained for 8 hr, thus yielding a spinel-type $MnCo_2O_4$ support.

Figure 4:
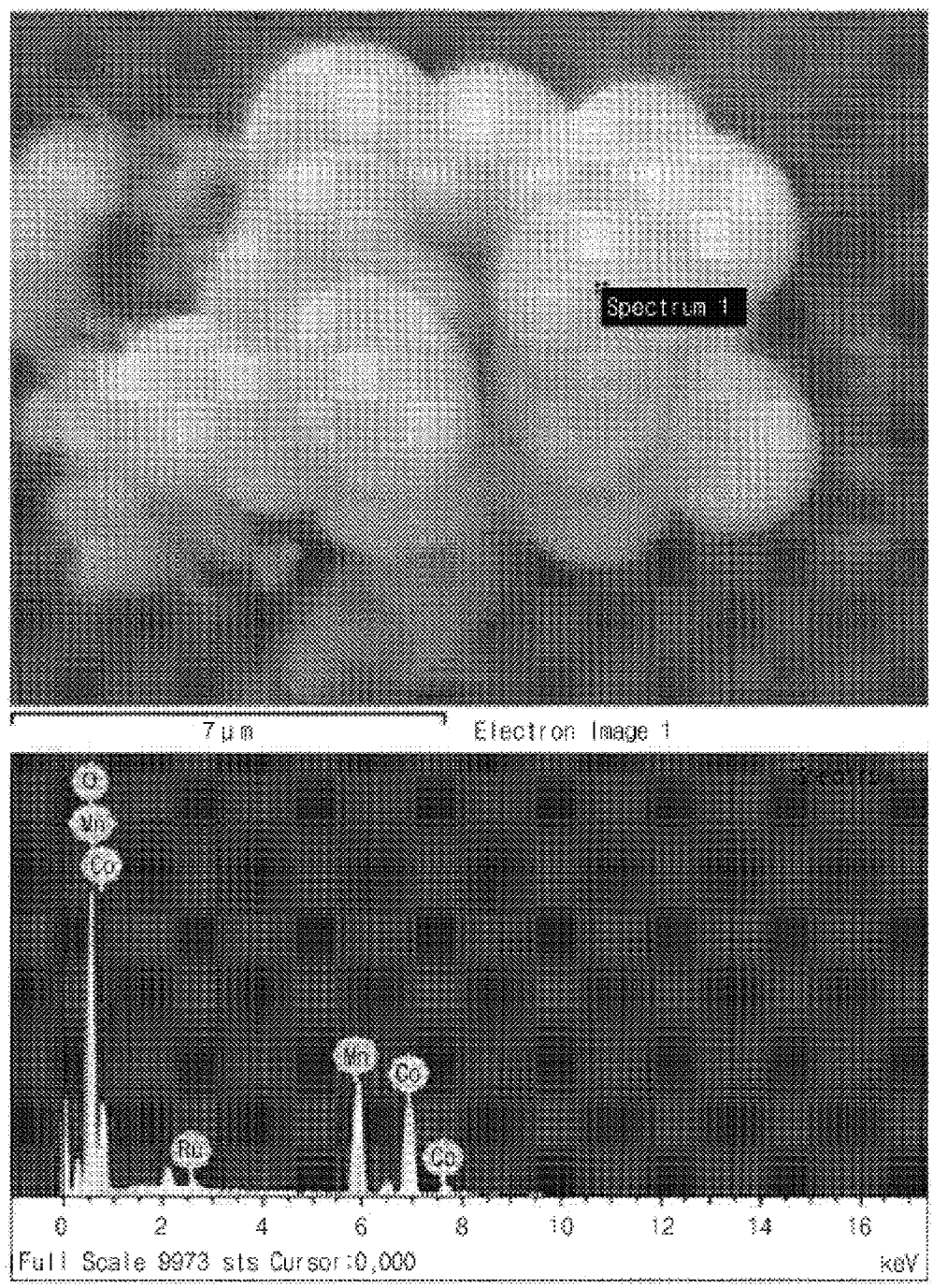
FIG. 4 shows the results of energy-dispersive X-ray (EDX/EDS) spectrometry performed on a catalyst configured such that Ru nanoparticles are incorporated into a spinel-type $MnCo_2O_4$ support according to an embodiment of the present invention.

Preparation of Catalyst Configured Such that Ruthenium Noble Metal Nanoparticles were Incorporated into Spinel-Type $MnCo_2O_4$ Support 5 g of the spinel-type $MnCo_2O_4$ support thus prepared and 0.432 g of $RuCl_3.3H_2O$, corresponding to 4.0 wt % of Ru based on the total amount of the catalyst, were placed in a two-neck round-bottom flask (100 mL) containing about 20 mL of water in a cooling bath. The mixture was stirred for 12 hr in an $N_2$ atmosphere. Thereafter, a $NaBH_4$ aqueous solution was added dropwise in the flask in an amount at least 10 times as large as the amount of $RuCl_3.3H_2O$ with stirring, after which stirring was performed at 500 rpm for one day at room temperature in an $N_2$ atmosphere so that the reaction was thoroughly carried out. Through the reaction, Ru( ) was reduced into Ru(0), thus forming nanoparticles. The catalyst thus obtained was filtered, separated and washed with ethanol. By performing the above procedures, the resulting catalyst was configured such that ruthenium noble metal nanoparticles were incorporated into the dried spinel-type $MnCo_2O_4$ support having a dark black color. In order to analyze the catalyst, energy-dispersive X-ray (EDX/EDS) spectrometry and Quantax 200 zero measurement were performed. The results are shown in FIG. 4. As shown in FIG. 4, the ruthenium noble metal can be confirmed to be incorporated into the spinel-type $MnCo_2O_4$ support.

Figure 5:
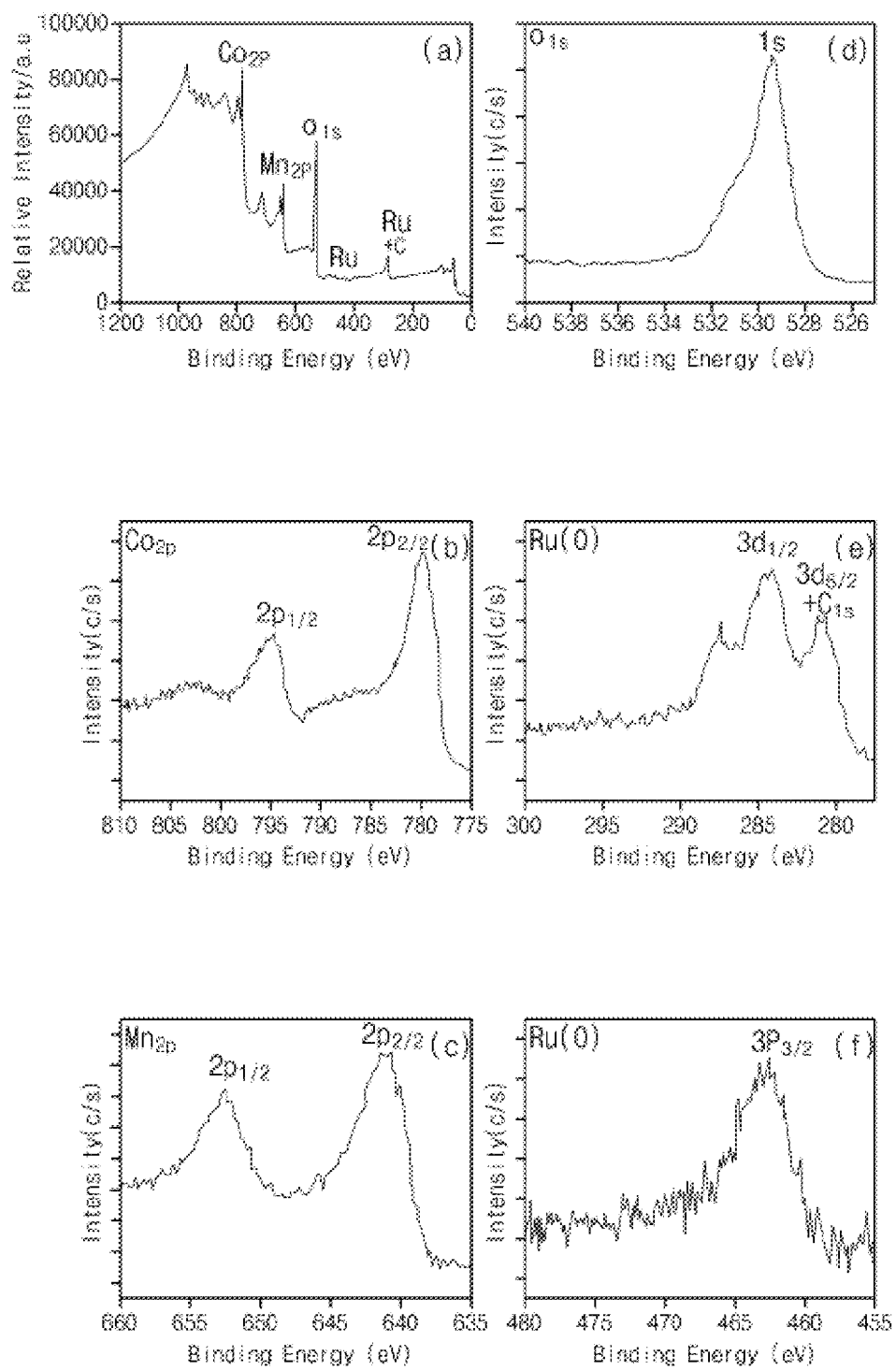
FIG. 5 shows the results of X-ray photoelectron spectroscopy (XPS) performed on the catalyst configured such that Ru nanoparticles are incorporated into a spinel-type $MnCo_2O_4$ support according to an embodiment of the present invention.

Moreover, as shown in FIG. 5, the catalyst was analyzed through X-ray photoelectron spectroscopy (XPS). In FIG. 5(a), Co, Mn, O and Ru were confirmed to be present, and in FIG. 5(d), O atoms were confirmed to be present within spinel lattices based on a 1s spectrum of O. In FIG. 5(f), the maximum peak of $3P_{3/2}$ of Ru was present in 455 to 480 eV, corresponding to the 3d region of Ru, from which Ru was confirmed to be metal particles.

Also, through HR TEM of the catalyst, the average diameter of Ru nanometal was determined to be 5 nm.

Oxidation from HMF into FDCA (Examples 1 to 4 and Comparative Examples 1 to 9)

Example 1

Figure 6:
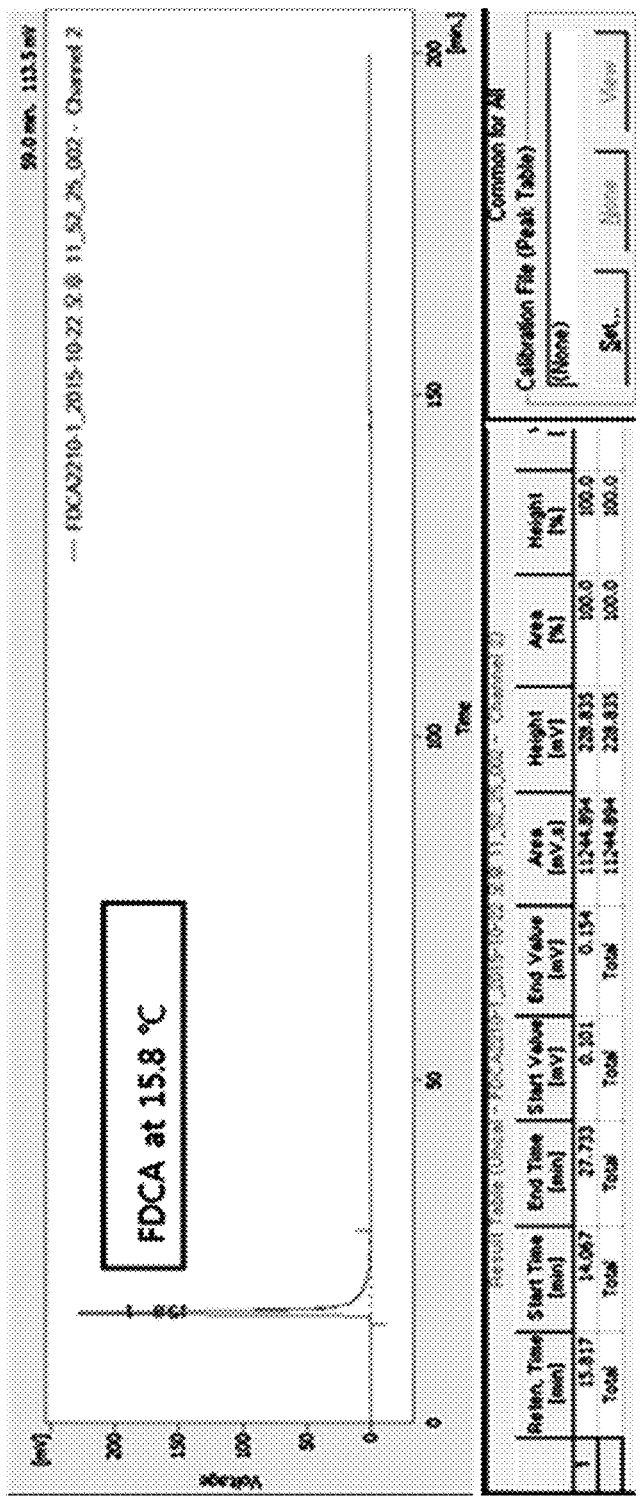
FIG. 6 shows the results of HPLC of a solid obtained after the preparation of FDCA using the catalyst of Example 1 according to the present invention.

A 100 mL stainless steel high-pressure reactor was provided with a magnetic stirrer and an electric heater. 5-hydroxymethylfurfural (HMF) (0.2513 g, 2.0 mmol) and 20 mL of a water solvent were placed therein, and the catalyst was added thereto, as shown in Table 1 below, after which mixing was performed at room temperature for at least 5 min with stirring at 100 rpm. While air was continuously supplied into the reactor, the temperature and pressure of the reactor were maintained at 120° C. and 150 psi, after which the final air pressure in the reactor was set to 350 psi with stirring at 600 rpm and the reaction was carried out at 120° C. for 10 hr. The pressure was adjusted using a back-pressure regulator connected to a reservoir tank so that the pressure in the reactor was maintained constant during the reaction. After completion of the reaction, the reaction mixture was cooled to room temperature and filtered, thus separating the solid product. The solid product thus separated was completely dried in a vacuum oven. The weight of FDCA produced after drying was measured, a portion thereof was dissolved in water containing $H_2SO_4$ (0.0005 M), and analysis was performed through HPLC (Agilent Technologies 1200 series, Bio-Rad Aminex HPX-87 H pre-packed column, and UV-detector), whereby the HMF conversion (C), FDCA yield (Y), and selectivity (S) of FDCA, FFCA and DFF were calculated using the following Equations (selectivity (S) of FFCA and DFF was calculated by being replaced with the yield of FFCA and DFF in the following Equation 3). The results of HPLC of Example 1 are shown in FIG. 6, and the calculated results are given in Table 1 below.

$$HMF\ \text{Conversion}\ (\%) = \frac{\text{mol of reacted}\ HMF}{\text{mol of added}\ HMF} \times 100 \quad [\text{Equation 1}]$$

$$FDCA\ \text{Yield}\ (\%) = \frac{\text{actual mol of produced}\ FDCA}{\text{theoretical mol of produced}\ FDCA} \times 100 \quad [\text{Equation 2}]$$

$$FDCA\ \text{Selectivity}\ (\%) = \frac{FDCA\ \text{yield}}{HMF\ \text{conversion}} \times 100 \quad [\text{Equation 3}]$$

Examples 2 to 4

The procedures were performed under the same conditions as in Example 1, with the exception that the amount of the catalyst, the reaction temperature and the reaction time were differently set. The results are shown in Table 1 below. FDCA was prepared at high yield even under acidic conditions of pH 3 to 4 in the vessel after initiation of the reaction in Examples 1 to 4.

TABLE 1

| | HMF (mmol) | HMF/metal molar ratio | Catalyst [metal (wt %)/support] | Temp. ° C. | Time (hr) | $C_{HMF}$, % | $Y_{FDCA}$, % | $S_{FDCA}$, % | $S_{FFCA}$, % | $S_{DFF}$, % |
|---|---|---|---|---|---|---|---|---|---|---|
| Example 1 | 1.0 | 10 | 4.0% Ru/$MnCo_2O_4$ | 120 | 10 | 99.9 | 92.6 | 92.6 | 0.0 | 0.0 |
| Example 2 | 1.0 | 25 | 1.8% Ru/$MnCo_2O_4$ | 120 | 10 | 99.0 | 87.9 | 88.8 | 4.7 | 0.0 |
| Example 3 | 2.0 | 85 | 1.8% Ru/$MnCo_2O_4$ | 150 | 8 | 99.9 | 81.9 | 82.0 | 3.3 | 0.0 |
| Example 4 | 2.0 | 150 | 1.8% Ru/$MnCo_2O_4$ | 150 | 5 | 100 | 43.7 | 43.7 | 29.8 | 0.5 |

Examples 5 to 8

The procedures were performed under the same conditions as in Example 1 (temperature: 120° C., reaction time: 10 hr), with the exception that the HMF/metal molar ratio was differently set. The results are shown in Table 2 below.

TABLE 2

|  | HMF (mmol) | HMF/metal molar ratio | Catalyst [metal (wt %)/support] | $C_{HMF}$, % | $Y_{FDCA}$, % | $S_{FDCA}$, % | $S_{FFCA}$, % | $S_{DFF}$, % |
| --- | --- | --- | --- | --- | --- | --- | --- | --- |
| Example 5 | 2.0 | 10 | 4.0% Ru/MnCo$_2$O$_4$ | 100 | 96.9 | 96.9 | 0.0 | 0.0 |
| Example 6 | 2.0 | 33.6 | 4.0% Ru/MnCo$_2$O$_4$ | 100 | 97.4 | 97.4 | 2.3 | 0.0 |
| Example 7 | 2.0 | 50 | 4.0% Ru/MnCo$_2$O$_4$ | 100 | 70.1 | 70.1 | 15.0 | 0.0 |
| Example 8 | 2.0 | 70 | 4.0% Ru/MnCo$_2$O$_4$ | 100 | 55.9 | 55.9 | 39.0 | 0.1 |

Examples 9 to 11

The procedures were performed under the same conditions as in Example 6 (temperature: 120° C., reaction time: 10 hr), with the exception that the air pressure was differently set. The results are shown in Table 3 below.

TABLE 3

|  | HMF (mmol) | HMF/metal molar ratio | Catalyst [metal (wt %)/support] | Pressure psi | $C_{HMF}$, % | $Y_{FDCA}$, % | $S_{FDCA}$, % | $S_{FFCA}$, % |
| --- | --- | --- | --- | --- | --- | --- | --- | --- |
| Example 9 | 2.0 | 33.6 | 4.0% Ru/MnCo$_2$O$_4$ | 150 | 100 | 67.3 | 67.3 | 21.7 |
| Example 10 | 2.0 | 33.6 | 4.0% Ru/MnCo$_2$O$_4$ | 250 | 100 | 86.9 | 86.9 | 4.3 |
| Example 6 | 2.0 | 33.6 | 4.0% Ru/MnCo$_2$O$_4$ | 350 | 100 | 97.4 | 97.4 | 2.3 |
| Example 11 | 2.0 | 33.6 | 4.0% Ru/MnCo$_2$O$_4$ | 450 | 100 | 98.7 | 98.7 | 0.0 |

Examples 12 to 14

The procedures were performed under the same conditions as in Example 6 (temperature: 120° C., reaction time: 10 hr, pressure: 350 psi), with the exception that the wt % of Ru nanometal based on the total weight of the catalyst of the invention was differently set. The results are shown in Table 4 below.

TABLE 4

|  | HMF (mmol) | Catalyst [metal (wt %)/support] | $C_{HMF}$, % | $Y_{FDCA}$, % | $S_{FDCA}$, % | $S_{FFCA}$, % | $S_{DFF}$, % |
| --- | --- | --- | --- | --- | --- | --- | --- |
| Example 12 | 2.0 | 1.0% Ru/MnCo$_2$O$_4$ | 87.4 | 17.8 | 20.4 | 54.2 | 13.4 |
| Example 13 | 2.0 | 2.0% Ru/MnCo$_2$O$_4$ | 90.8 | 60.1 | 66.2 | 3.3 | 1.2 |
| Example 6 | 2.0 | 4.0% Ru/MnCo$_2$O$_4$ | 100 | 97.4 | 97.4 | 2.3 | 0.0 |
| Example 14 | 2.0 | 10.0% Ru/MnCo$_2$O$_4$ | 100 | 98.4 | 98.4 | 0.0 | 0.0 |

Example 15

A spinel-type support, in which the molar ratio of Co:Mn was 1:2, was prepared using (CH$_3$COO)$_2$Co.4H$_2$O and (CH$_3$COO)$_2$Mn.4H$_2$O at a molar ratio of 1:2, and 4 wt % of Ru nanometal was incorporated into the support, after which the procedures were performed in the same manner as in Example 6 (temperature: 120° C., reaction time: 10 hr, pressure: 350 psi). The results are shown in Table 5 below.

TABLE 5

|  | HMF (mmol) | HMF/metal molar ratio | Catalyst [metal (wt %)/support] | $C_{HMF}$, % | $Y_{FDCA}$, % | $S_{FDCA}$, % | $S_{FFCA}$, % | $S_{DFF}$, % |
| --- | --- | --- | --- | --- | --- | --- | --- | --- |
| Example 6 | 2.0 | 33.6 | 4.0% Ru/MnCo$_2$O$_4$ | 100 | 97.4 | 97.4 | 2.3 | 0.0 |
| Example 15 | 2.0 | 33.6 | 4.0% Ru/CoMn$_2$O$_4$ | 98.8 | 70.1 | 70.9 | 27.3 | 0.0 |

Example 16

The procedures were performed under the same conditions as in Example 6, with the exception that AMF (5-acetoxymethyl-2-furfural) was used as the substrate in lieu of HMF. The results are shown in Table 6 below. FDCA was produced at high yield even when AMF was used as the substrate.

TABLE 6

| | Substrate (mmol) | HMF/metal molar ratio | Catalyst [metal (wt %)/support] | $C_{HMF}$, % | $Y_{FDCA}$, % | $S_{FDCA}$, % | $S_{FFCA}$, % | $S_{DFF}$, % |
|---|---|---|---|---|---|---|---|---|
| Example 16 | AMF 2.0 | 33.6 | 4.0% Ru/MnCo$_2$O$_4$ | 100 | 95.7 | 95.7 | 2.5 | 0 |

Comparative Example 1

The procedures were performed under the same conditions as in Example 1, with the exception that a catalyst composed exclusively of MnCo$_2$O$_4$ without Ru metal was used and the temperature and reaction time were differently set. The results are shown in Table 7 below.

TABLE 7

| | HMF (mmol) | Catalyst [metal (wt %)/support] | Temp. ° C. | Time (hr) | $C_{HMF}$, % | $Y_{FDCA}$, % | $S_{FDCA}$, % | $S_{FFCA}$, % | $S_{DFF}$, % |
|---|---|---|---|---|---|---|---|---|---|
| Comparative Example 1 | 2.0 | MnCo$_2$O$_4$ | 150 | 5 | 42.8 | 2.0 | 4.7 | 10.8 | 24.9 |

As is apparent from the above Table, when the catalyst composed exclusively of the MnCo$_2$O$_4$ support without Ru was used, unlike the catalyst of Examples of the present invention, the HMF conversion, FDCA yield, and FDCA selectivity were significantly decreased.

Comparative Examples 2 and 3

The procedures were performed under the same conditions as in Example 1, with the exception that Au metal nanoparticles and a MnCo$_2$O$_4$ support were used as shown in Table 8 below, and the reaction time and temperature were differently set. The results are shown in Table 8 below.

TABLE 8

| | HMF (mmol) | HMF/metal molar ratio | Catalyst [metal (wt %)/support] | Temp. ° C. | Time (hr) | $C_{HMF}$, % | $Y_{FDCA}$, % | $S_{FDCA}$, % | $S_{FFCA}$, % | $S_{DFF}$, % |
|---|---|---|---|---|---|---|---|---|---|---|
| Comparative Example 2 | 2.0 | 250 | 2.1% Au/MnCo$_2$O$_4$ | 150 | 5 | 67.2 | 8.9 | 13.3 | 21.2 | 11.6 |
| Comparative Example 3 | 4.0 | 500 | 2.1% Au/MnCo$_2$O$_4$ | 150 | 2 | 88.5 | 0.04 | — | — | — |

As is apparent from the above Table, when the MnCo$_2$O$_4$ support containing Au was used as the catalyst, unlike the catalyst of Examples of the present invention, the FDCA yield was significantly decreased.

Comparative Examples 4 to 7

The procedures were performed under the same conditions as in Example 6, with the exception that a catalyst comprising an Au metal/CeO$_2$ support was used and some of the test conditions were differently set, as shown in Table 9 below. In Comparative Example 6, a solvent mixture of acetic acid and methanol at 8:2 was used, in lieu of the water solvent.

TABLE 9

| | HMF (mmol) | Catalyst [metal (wt %)/support] | Temp. °C. | Time (hr) | $C_{HMF}$, % | $Y_{FDCA}$, % | $S_{FDCA}$, % | $S_{FFCA}$, % | $S_{DFF}$, % |
|---|---|---|---|---|---|---|---|---|---|
| Comparative Example 4 | 2.0 | 2.1% Au/CeO$_2$ | 150 | 2 | 68.8 | 1.7 | 2.5 | 3.7 | 8.0 |
| Comparative Example 5 | 2.0 | 2.1% Au/CeO$_2$ | 150 | 5 | 93.8 | 2.2 | 2.3 | 1.5 | 0.9 |
| Comparative Example 6 | 8.0 | 2.1% Au/CeO$_2$ | 150 | 2 | 45.4 | 0.01 | 0.03 | 0.03 | 13.7 |
| Comparative Example 7 | 4.0 | 2.1% Au/CeO$_2$ | 150 | 2 | 81.05 | 0.01 | — | — | — |

*at 400° C., Au was reduced under H$_2$ flow, 2.1% Au/CeO$_2$

As is apparent from the above Table, when the catalysts of Comparative Examples 4 to 7 including the support and the metal particles different from those of the catalyst of the present invention were used, the conversion, yield and selectivity were significantly lowered even at high reaction temperatures compared to Examples 1 to 6 according to the present invention. In particular, the 2.1% Au/CeO$_2$ catalyst of Comparative Examples 4 to 7 was produced in a manner in which Au ions were reduced under strongly basic conditions (pH of about 10 or more, NaOH solution), incorporated into CeO$_2$ and dried, whereby the catalyst itself was made to be strongly basic. When comparing the solvent of Comparative Example 6 (solvent, acetic acid:methanol=8:2) with the solvent of Comparative Examples 4, 5 and 7 (solvent, water), Comparative Example 6, using the acidic solvent, exhibited drastically lowered HMF conversion and very low FDCA yield and selectivity, from which the above catalyst was confirmed to be basic.

Comparative Example 8

The procedures were performed under the same conditions as in Example 1, with the exception that a Ru metal/MgAl$_2$O$_4$ support was used as the catalyst.

As described above, in Comparative Example 8 using the support (MgAl$_2$O$_4$) other than the spinel support of the present invention, even when the Ru catalyst was used in the same amount, the FDCA selectivity did not reach 60%, unlike Example 1 of the present invention, and the yield was also remarkably low.

Comparative Example 9

The procedures were performed under the same conditions as in Example 6, with the exception that a Ru metal/carbon was used as the catalyst and the base materials Na$_2$CO$_3$ and NaHCO$_3$ were placed in the reactor. The pH in the reactor after initiation of the reaction of Comparative Example 9 was 7 to 8. Furthermore, the procedures were performed under the same conditions (base-free conditions) as in Example 6 using the same catalyst (Ru metal/carbon).

TABLE 11

| | HMF (mmol) | HMF/metal molar ratio | Catalyst [metal (wt %)/support] | Base material | Time (hr) | $C_{HMF}$, % | $Y_{FDCA}$, % | $S_{FDCA}$, % | $S_{FFCA}$, % | $S_{DFF}$, % |
|---|---|---|---|---|---|---|---|---|---|---|
| Comparative Example 9 | 2.0 | 33.3 | 4% Ru/carbon | NaHCO$_3$ | 10 | 100 | 85.1 | 85.1 | 10.1 | 0.9 |
| Comparative Example 10 | 2.0 | 33.3 | 4% Ru/carbon | — | 10 | 50.4 | 35.1 | 69.9 | 15.3 | 0 |

As is apparent from Table 11, when the Ru metal/carbon support was used under basic conditions, the FDCA yield was low compared to Example 6 of the present invention, and very poor results were obtained under base-free conditions.

Comparative Example 10 to 12

The procedures were performed as shown in Table 8 in the same manner as in Example 6, with the exception that different kinds of supports were used, as shown in Table 12 below.

TABLE 10

| | HMF (mmol) | HMF/metal molar ratio | Catalyst [metal (wt %)/support] | Temp. °C. | Time (hr) | $C_{HMF}$, % | $Y_{FDCA}$, % | $S_{FDCA}$, % | $S_{FFCA}$, % | $S_{DFF}$, % |
|---|---|---|---|---|---|---|---|---|---|---|
| Comparative Example 8 | 1.0 | 33.3 | 4% Ru/MgAl$_2$O$_4$ | 120 | 10 | 90.5 | 53.7 | 59.4 | 10.5 | 1.0 |

TABLE 12

| | HMF (mmol) | HMF/metal molar ratio | Catalyst [metal (wt %)/support] | $C_{HMF}$, % | $Y_{FDCA}$, % | $S_{FDCA}$, % | $S_{FFCA}$, % | $S_{DFF}$, % |
|---|---|---|---|---|---|---|---|---|
| Example 6 | 2.0 | 33.6 | 4.0% Ru/MnCo$_2$O$_4$ | 100 | 100 | 97.4 | 2.3 | 0.0 |
| Comparative Example 11 | 2.0 | 33.6 | 4.0% Ru/CoO | 91.1 | 17.8 | 19.5 | 54.2 | 13.4 |
| Comparative Example 12 | 2.0 | 33.6 | 4.0% Ru/MnCo$_2$CO$_3$ | 100 | 69.9 | 69.9 | 15.5 | 0.0 |
| Comparative Example 13 | 2.0 | 33.6 | 4.0% Ru/MnO$_2$ | 98.8 | 31.1 | 31.5 | 37.3 | 1.2 |

As is apparent from Table 12, even when the Ru nano metal was used in the same amount, the FDCA yield and selectivity were remarkably lowered in Comparative Examples 11, 12 and 13, which did not include the support (MnCo$_2$O$_4$) according to an embodiment of the present invention.

What is claimed is:

1. A carboxylation catalyst which catalyzes carboxylation of a furan-based compound containing a hydroxyl group and a carbonyl group or a derivative thereof to prepare 2,5-furandicarboxylic acid (FDCA), comprising:
   a spinel support selected from the group consisting of MnCo$_2$O$_4$, CoMn$_2$O$_4$, and combinations thereof; and
   noble metal nanoparticles incorporated into the spinel support.

2. The carboxylation catalyst of claim 1, wherein the spinel support has an average particle size (D$_{50}$) of 2.0 to 4.0 µm.

3. The carboxylation catalyst of claim 1, wherein the noble metal is selected from the group consisting of platinum, palladium, ruthenium, and combinations thereof.

4. The carboxylation catalyst of claim 3, wherein the noble metal is ruthenium.

5. The carboxylation catalyst of claim 1, wherein the furan-based compound is 5-hydroxymethylfurfural (HMF).

6. The carboxylation catalyst of claim 1, wherein the derivative of the furan-based compound is 5-acetoxymethyl-2-furfural (AMF).

7. The carboxylation catalyst of claim 1, wherein the noble metal nanoparticles are used in an amount of 0.1 to 10 wt % based on total weight of the catalyst.

8. A method of preparing 2,5-furandicarboxylic acid (FDCA), comprising:
   providing a carboxylation catalyst configured such that noble metal nanoparticles are incorporated into a spinel support selected from the group consisting of MnCo$_2$O$_4$, CoMn$_2$O$_4$, and combinations thereof; and
   carboxylating a furan-based compound containing a hydroxyl group and a carbonyl group or a derivative thereof using the carboxylation catalyst.

9. The method of claim 8, wherein the furan-based compound is 5-hydroxymethylfurfural (HMF).

10. The method of claim 8, wherein the derivative of the furan-based compound is 5-acetoxymethyl-2-furfural (AMF).

11. The method of claim 8, wherein the noble metal nanoparticles are selected from the group consisting of platinum, palladium, ruthenium, and combinations thereof.

12. The method of claim 8, wherein oxidation of the furan-based compound is carried out under conditions of a temperature of 100 to 200° C., an air pressure of 80 to 1000 psi, and a reaction time of 3 to 12 hr.

13. The method of claim 8, wherein a molar ratio of the noble metal nanoparticles to the furan-based compound is 1:5-200.

14. The method of claim 8, wherein oxidation of the furan-based compound is carried out in a single vessel using water as a solvent under base-free conditions.

15. The method of claim 9, wherein the 5-hydroxymethylfurfural (HMF) is obtained from biomass containing cellulose or polysaccharides.

16. The method of claim 8, wherein the noble metal nanoparticles are used in an amount of 0.1 to 10 wt % based on a total weight of the catalyst.

* * * * *